(12) United States Patent
Ku

(10) Patent No.: US 6,231,605 B1
(45) Date of Patent: May 15, 2001

(54) POLY(VINYL ALCOHOL) HYDROGEL

(75) Inventor: David N. Ku, Atlanta, GA (US)

(73) Assignee: Restore Therapeutics, Atlanta, GA (US)

(*) Notice: Subject to any disclaimer, the term of this patent is extended or adjusted under 35 U.S.C. 154(b) by 0 days.

(21) Appl. No.: 09/271,032

(22) Filed: Mar. 17, 1999

Related U.S. Application Data

(63) Continuation of application No. 08/932,029, filed on Sep. 17, 1997, now Pat. No. 5,981,826.
(60) Provisional application No. 60/045,875, filed on May 5, 1997.

(51) Int. Cl.[7] ................ A61F 2/02; A61F 2/30; A61F 2/44
(52) U.S. Cl. .................... 623/11.11; 623/23.58; 623/18.11; 623/17.11
(58) Field of Search ................ 623/18, 16, 901, 623/11

(56) References Cited

U.S. PATENT DOCUMENTS

| | | | |
|---|---|---|---|
| 5,258,042 | 11/1993 | Mehta | 623/66 |
| 5,260,066 | 11/1993 | Wood et al. | 424/447 |
| 5,288,503 | 2/1994 | Wood et al. | 424/497 |
| 5,314,478 | 5/1994 | Oka et al. | 623/18 |
| 5,326,364 | 7/1994 | Clift, Jr. et al. | 623/21 |
| 5,458,643 | 10/1995 | Oka et al. | 623/18 |
| 5,458,645 | 10/1995 | Bertin | 623/20 |
| 5,700,289 * | 12/1997 | Breitbart et al. | 623/16 |
| 5,795,353 | 8/1998 | Felt | 623/18 |
| 5,847,046 * | 12/1998 | Jiang et al. | 524/42 |

* cited by examiner

Primary Examiner—Corrine McDermott
Assistant Examiner—Choon P. Koh
(74) Attorney, Agent, or Firm—Lyon & Lyon LLP

(57) ABSTRACT

The present invention relate to a poly(vinyl alcohol) hydrogel construct having a wide range of mechanical strengths for use as a human tissue replacement. The hydrogel construct may include a tissue scaffolding, a low bearing surface within a joint, or any other structure which is suitable for supporting the growth of tissue.

5 Claims, No Drawings

POLY(VINYL ALCOHOL) HYDROGEL

RELATED APPLICATIONS

This application is a continuation of application Ser. No. 08/932,029, filed on Sep. 17, 1997 which issued as U.S. Pat. No. 5,981,826 on Nov. 9, 1999 and which claims priority to provisional application Ser. No. 60/045,875, filed on May 5, 1997, which is incorporated herein by reference in its entirety.

FIELD OF THE INVENTION

The present invention relates generally to hydrogel materials. More specifically, the present invention relates to a poly(vinyl alcohol) ("PVA") hydrogel.

DESCRIPTION OF THE PRIOR ART

Most tissues of the living body include a large weight percentage of water. Therefore, in a selection of a prosthesis, a hydrous polymer (hydrogel) is considered to be superior in biocompatibility as compared to nonhydrous polymers. Although hydrogels do less damage to tissues than nonhydrous polymers, conventional hydrogels have historically included a serious defect in that they are inferior in mechanical strength. For that reason, the use of hydrogels has been extremely limited in the past.

Artisans have proposed a number of hardening means for improving mechanical strength. Some hardening means include treating the hydrogel with a cross-linking agent such as formaldehyde, ethylaldehyde, glutaraldehyde, terephthalaldehyde or hexamethylenediamine. Unfortunately, however, it is well known that those treatments decrease the biocompatibility of the hydrogel biomaterial. One example of a popular hydrogel which has been proposed for use as a biomaterial is PVA.

Numerous references generally describe the process of freezing and thawing PVA to create a hydrogel: Chu et al., *Poly(vinyl alcohol) Cryogel: An Ideal Phantom Material for MR Studies of Arterial Elasticity*, Magnetic Resonance in Medicine, v. 37, pp. 314–319 (1997); Stauffer et al., *Poly (vinyl alcohol) hydrogels prepared by freezing-thawing cyclic processing*, Polymer, v.33, pp. 3932–3936 (1992); Lozinsky et al., *Study of Cryostructurization of polymer systems*, Colloid & Polymer Science, v. 264, pp. 19–24 (1986); Watase and Nishinari, *Thermal and rheological properties of poly(vinyl alcohol) hydrogels prepared by repeated cycles of freezing and thawing*, Makromol. Chem., v. 189, pp. 871–880 (1988). The disclosure from these references is hereby incorporated by reference.

Another such reference is U.S. Pat. No. 4,734,097, issued to Tanabe et al. on Mar. 29, 1988 ("Tanabe"). Tanabe proposes the construct of a molded hydrogel obtained by pouring an aqueous solution containing not less than 6% by weight of a polyvinyl alcohol which has a degree of hydrolysis not less than 97 mole percent and an average polymerization degree of not less than 1,100 into a desired shape of a vessel or mold, freeze molding an aqueous solution in a temperature lower than minus 5° C., then partially dehydrating the resulting molded product without thawing it up to a percentage of dehydration not less than 5 weight percent, and if required, immersing the partially hydrated molded part into water to attain a water content thereof in the range of 45 to 95 weight percent.

The disadvantage to Tanabe et al. is that it necessarily requires a step of dehydration in preparing the PVA hydrogel. There are several disadvantages associated with the dehydration step. First, the dehydration step adds additional time and capital expense associated with machinery which must accomplish the dehydration step. Additionally, dehydration may denature bioagents included in the hydrogel.

Hyon et al., U.S. Pat. No. 4,663,358 is directed to producing PVA hydrogels having a high tensile strength and water content. However, this patent is not directed to hydrating the PVA with water alone, but rather uses a mixture of water and an organic solvent such as dimethyl sulfoxide (DMSO). DMSO is recognized as an initiator of carcinogenicity. Residual amounts of organic solvents in the resultant PVA hydrogel render such products undesirable for biomedical applications, particularly where the hydrogel is to be used for long term implants within the body.

With the foregoing disadvantages of the prior art in mind, it is an object of the present invention to provide a biocompatible PVA hydrogel which includes a mechanical strength range sufficient for a wide variety of applications as biomaterial.

It is another object of the present invention to provide a method for producing the PVA hydrogel which precisely controls the mechanical strength thereof, and which eliminates any dehydration step prior to implantation.

Other objects, features and advantages of the present invention will become apparent upon reading the following specification.

SUMMARY OF THE INVENTION

Generally speaking, the present invention relates to a novel poly(vinyl alcohol) ("PVA") hydrogel tissue replacement construct and a process for making the construct.

More specifically, the present invention relates to a non-dehydrated PVA hydrogel construct which is capable of being molded into a number of shapes, and which is capable of retaining a wide range of mechanical strengths for various applications.

The PVA hydrogel may comprise a PVA polymer starting material in the form of a dry powder wherein the degree of polymerization of the PVA may range approximately 500 to 3,500. The tissue replacement in accordance with the present invention may include approximately 2 to approximately 40 parts by weight PVA and approximately 98 to 60 parts by weight water. Additionally, the hydrogel may include an isotonic saline solution substitute for water to prevent osmotic imbalances between the tissue replacement and surrounding tissues. The replacement may also include a number of bioactive agents including, but not limited to, heparin, growth factors, collagen crosslinking inhibitors such as $\beta$-aminopropeonitrile ($\beta$APN), matrix inhibitors, antibodies, cytokines, integrins, thrombins, thrombin inhibitors, proteases, anticoagulants and glycosaminoglycans.

A process in accordance with the present invention involves mixing water with the PVA crystal to obtain a non-dehydrated PVA hydrogel, thereby eliminating the dehydration step prior to implantation. More specifically, the present invention involves freezing and thawing the PVA/water mixture to create an interlocking mesh between PVA polymer molecules to create the PVA hydrogel. The freezing and thawing step may be performed at least twice, with mechanical strength of the PVA hydrogel increasing each time the freezing and thawing step is performed. The process may include the further steps of pouring the PVA/water mixture into a mold, freezing the mixture, and the thawing the mixture to obtain a non-dehydrated construct. Additionally, the process may also include the step of removing the construct from the mold, immersing the construct in water, freezing the construct while immersed in water and thawing the construct while immersed in water to increase the mechanical strength of the construct. The process may also include the steps of adding bioactive agents to the hydrogel.

Because it can be manufactured to be mechanically strong, or to possess various levels of strength among other physical properties, it can be adapted for use in many applications. The hydrogel also has a high water content which provides desirable properties in numerous applications. For example, the hydrogel tissue replacement construct is especially useful in surgical and other medical applications as an artificial material for replacing and reconstructing soft tissues in humans and other mammals. Soft tissue body parts which can be replaced or reconstructed by the hydrogel include, but are not limited to, vascular grafts, heart valves, esophageal tissue, skin, corneal tissue, cartilage, meniscus, and tendon. Furthermore, the hydrogel may also serve as a cartilage replacement for anatomical structures including, but not limited to an ear or nose. The inventive hydrogel may also serve as a tissue expander. Additionally, the inventive hydrogel may be suitable for an implantable drug delivery device. In that application, the rate of drug delivery to tissue will depend upon hydrogel pore size and degree of intermolecular meshing resulting from the freeze/thaw device. The rate of drug delivery increases with the number of pores and decreases with an increasing degree of intermolecular meshing from an increased number of freeze/thaw cycles. The inventive hydrogel may consist essentially of a PVA polymer and about 20% to about 95% water, by weight. The mechanical and thermal properties of PVA hydrogel constructs, for biomedical applications in particular, are important to the performance of the constructs, as are the hydrogel's swelling properties and coefficient of friction. The structures produced by the novel process of this invention have advantageous properties in each of these areas. The process of the present invention produces crystallites in the PVA hydrogel polymer which leads to unique and enhanced mechanical properties, thermal behavior and increased fatigue strength.

The tensile properties of the PVA hydrogel of the present invention may be characterized by its deformation behavior. The freedom of motion of the PVA polymer of the present invention is retained at a local level while the network structure produced by the process of this invention prevents large-scale movements or flow. Rubbery polymers tend to exhibit a lower modulus, or stiffness, and extensibilities which are high. Glassy and semi-crystalline polymers have higher moduli and lower extensibilities. The tensile and compressive properties of the construct of the present invention are reflected by a modulus of elasticity of between about 0.1 and about 20 megaPascals, thus producing a hydrogel having excellent strength and flexibility characteristics.

In the liquid or melt state, a non-crystalline polymer possesses enough thermal energy for long segments of each polymer to move randomly, called Brownian motion. As the mixture cooled, the temperature is eventually reached at which all long range segmental motion ceases. This temperature at which segmental motions ceases, which is a function of both the polymer material and how it is processed, is called the glass transition temperature. Experimentally, this glass transition temperature is often defined by incrementally increasing the temperature of the hydrogel until sequential reaction begins and energy is absorbed. The glass transition properties of the PVA hydrogel construct provided by the method of the present invention is greater than about 40 degrees Celsius.

An integral part of the physical behavior of PVA hydrogel constructs here disclosed is their swelling behavior in water, because the process of this invention requires that the PVA be immersed in water in order to yield the final, solvated network structure. The thermodynamic swelling force is counter balanced by the retractive force of the hydrogel structure and, in the process of this invention, constrained by the mold in which the hydrogel is placed. These retractive forces of the hydrogel are described by the Flory rubber elasticity theory and its variations. Equilibrium is reached, in water and at a particular temperature, when the thermodynamic swelling force is equal to the retractive force. The swelling properties of the PVA hydrogel construct of this invention are such that the dimensions of the construct are increased by swelling by less than about 20%, and preferably less than about 5%, when immersed in water. Alternatively, the shrinkage is correspondingly less than 20%, and preferably less than about 5%. When the PVA hydrogel of this invention is used in applications such as biomedical applications, for example as a knee joint resurfacing agent, low friction is desirable. The construct of the present invention has a coefficient of friction of less than about 0.1. For a general description of the physical properties of polymers and their properties see, Biomaterials Science an Introduction to Materials in Medicine, Ratner, et al. (Academic Press 1996), pp. 52–53 and 62.

The hydrogel is especially suitable for vascular grafts and heart valve replacements, because the hydrogel is thromboresistant, and because of the particular mechanical and physiological requirements of vascular grafts when implanted into the body. The hydrogel may also be used for contact lenses, as a covering for wounds such as burns and abrasions, as a nerve bridge, as a ureteral stent, and in other applications wherein a mechanically strong material is preferred. Because of its low coefficient of friction, the hydrogel may also be used as a coating to reduce friction between surfaces, such as on a catheter.

Other objects, features and advantages of the present invention will become apparent upon reading the following specification, when taken in conjunction with the accompanying examples.

Reference will now be made in detail to the description of the invention. While the invention will be described in connection with specific examples, there is no intent to limit it to the embodiment or embodiments disclosed therein. On the contrary, the intent is to cover all alternatives, modifications and equivalents included within the spirit and scope of the invention as defined by the appended claims.

DETAILED DESCRIPTION OF THE PREFERRED EMBODIMENTS

In a preferred embodiment, a process in accordance with the present invention produces the hydrogel in a two stage process. In the first stage a mixture of poly(vinyl alcohol) and water is placed in a mold, and repeatedly frozen and thawed, in cycles, until a suitable hydrogel is obtained. In a second stage, the hydrogel is removed from the mold, placed in water, and undergoes at least one other freeze-thaw cycle until desirable mechanical properties are achieved. In the first stage, a series of sequential steps is employed comprising: (i) mixing water with poly(vinyl alcohol) to obtain a poly(vinyl alcohol)/water mixture; (ii) freezing the mixture; (iii) thawing the mixture; and (iv) repeating the freeze and thaw steps, as necessary, until a poly(vinyl alcohol) hydrogel having the desired physical properties is obtained. If necessary, the second stage may then be employed.

Poly(vinyl alcohol) useful for the invention is typically obtained as a dry powder or crystal, and can vary based upon several factors, including molecular weight, degree of polymerization, and degree of saponification (or hydrolysis). The molecular weight of the poly(vinyl alcohol) can vary, and can be chosen depending upon the particular application envisioned for the hydrogel. Generally, increasing the molecular weight of the poly(vinyl alcohol) increases the tensile strength and tensile stiffness, and thereby improves the properties of constructs such as vascular grafts, wherein increased strength is desirable. In other applications, such as a nerve bridge, lower molecular weight poly(vinyl alcohol) can be employed because lower tensile strength and lower tensile stiffness are desirable. Poly(vinyl alcohol) having an average molecular weight of from about 11,000 to 500,000 is preferred for practicing the invention. Poly(vinyl alcohol) having an average molecular weight of from about 85,000 to 186,000 is even more preferred for practicing the invention, especially when producing vascular grafts, and poly(vinyl alcohol) having an average molecular weight of from about 124,000 to 186,000 is especially preferred.

The average degree of polymerization for preferred poly(vinyl alcohol)s generally ranges from about 500 to 3500, and poly(vinyl alcohol) having a degree of polymerization of from about 2700 to 3500 is especially preferred. Preferred poly(vinyl alcohol) typically has a degree of saponification (or hydrolysis) in excess of 80%, more preferred poly(vinyl alcohol) is saponified (or hydrolyzed) in excess of about 98%, and even more preferred poly(vinyl alcohol) is saponified (or hydrolyzed) in excess of 99%.

The water that is mixed with the poly(vinyl alcohol) preferably undergoes deionization, reverse osmosis and ultra filtered to minimize the potential for any contamination of the poly(vinyl alcohol). The mixture is preferably prepared by mixing from about 2 to about 40 parts by weight poly(vinyl alcohol) with about 98 to 60 parts by weight water. The concentration of the poly(vinyl alcohol) contributes to the stiffness of the hydrogel and can thus be chosen depending upon the stiffness of the material one desires to obtain. A more preferable mixture is obtained by mixing from about 10 to about 30 parts poly(vinyl alcohol) with from about 70 to about 90 parts by weight water, and an especially preferred mixture is obtained by mixing about 25 parts poly(vinyl alcohol) with about 75 parts by weight water. Isotonic saline (0.9% weight to volume in water) or an isotonic buffered saline may be substituted for water to prevent osmotic imbalances between the material and surrounding tissues if the hydrogel is to be used as a soft tissue replacement.

After the poly(vinyl alcohol) and water are mixed, it is often necessary to process the mixture to ensure that the poly(vinyl alcohol) is adequately solubilized. Suitable solubilization processes are generally known in the art and include, for example, heating the mixture, altering the pH of the mixture, adding a solvent to the mixture, subjecting the mixture to external pressure, or a combination of these processes. A preferred method is to heat the mixture at a temperature of about 95° C.–120° C., for a period of time not less than 15 minutes and the one way of doing this, is an autoclave which also allows us to sterilize the mixture before further processing.

After the mixture has been prepared, air bubbles that may have become entrapped in the mixture should be removed. The solution can be allowed to sit for a period of time, preferably at an elevated temperature, to allow the air bubbles to rise out of solution. The mixture can also be placed in a sterile vacuum chamber for a short time to bring the bubbles out of solution. The mixture can also be centrifuged at an elevated temperature to bring the bubbles out of solution.

Once prepared, the mixture can be poured into one or more pre-sterilized molds. If needed, the solution in the mold can be allowed to sit upright, or subjected to a vacuum in a vacuum chamber, to remove undesirable air bubbles. The shape and size of the mold may be selected to obtain a hydrogel of any desired size and shape. Vascular grafts, for example, can be produced by pouring the poly(vinyl alcohol)/water mixture into an annular mold. The size and dimensions of the mold can be selected based upon the location for the graft in the body, which can be matched to physiological conditions using normal tables incorporating limb girth, activity level, and history of ischemia. Suitable annular molds for producing vascular grafts would include Y-shaped molds, which can be used to produce grafts having vascular branching. The hydrogel can also be processed by cutting or otherwise forming the hydrogel into the desired form after it has been produced. Although not necessary, molds are preferably capped or sealed to prevent dehydration and to preserve sterility. Typically, the mold is not filled entirely with the solution in order to accommodate for the expansion of the hydrogel during freezing.

Molds for practicing the invention can be comprised of many suitable materials that will not react with the poly(vinyl alcohol) solution, that will maintain integrity over the required temperature range, and that will allow the hydrogel to be removed without damaging the hydrogel. Suitable materials include but are not limited to natural and synthetic resins, natural and synthetic polymers (including those based upon polycarbonates, acrylates and methacrylates, and poly(vinyl alcohol)), glass, steel, aluminum, brass, and copper, among other materials. Outer molds that are compliant and elastic result in a more complete gelling and better physical properties than molds that are stiff. High pressure in the frozen poly(vinyl alcohol) reduces the stiffness of the resulting gel, and compliant molds reduce the pressure on the poly(vinyl alcohol) while it is frozen. Preferred annular molds are constructed from smooth stainless steel or poly(vinyl chloride) tubes around stainless steel mandrels. More preferred annular molds are constructed of compliant poly(vinyl chloride) or other plastic tubes around stainless steel mandrels.

After the mixture has been poured into the mold, and the mold has been sealed, it is frozen to a temperature preferably below about −5° C., and more preferably below about −20° C. The mixture should preferably be frozen for at least 1 hour, including freezing time, more preferably at least 4 hours, and most preferably from about 4 to about 16 hours. In contrast to methods cited in the prior art, no dehydration step is required, and in a preferred embodiment dehydration is not employed because of the importance of hydration to the final product.

After the mixture has been frozen, the temperature of the mixture is raised and the mixture thawed. It is generally preferable to raise the temperature to from about 5 to about 35° C., and to thaw the solution at such temperature for a period of time of about 1 hour or more, and more preferably at least 4 hours, and most preferably from about 4 to about 16 hours, including thawing time and time at such temperature. It is especially preferable to raise the temperature to about 25° C., and to thaw the mixture at such temperature for about 12 hours. Because the hydrogel is solubilized at higher temperatures, the temperature of the mixture should not generally be raised above about 45° C.

After the mixture has been frozen and thawed once under the foregoing conditions, the process may be repeated, although the exact process conditions need not be repeated for each freeze/thaw cycle. Generally, increasing the number of freeze/thaw cycles increases the tensile strength and tensile stiffness of the hydrogel, and can be implemented for applications such as vascular grafts wherein higher strength and stiffness are desired. In other applications, such as a nerve tube, lower numbers of freeze/thaw cycles can be employed because lower tensile strength and lower tensile stiffness are desirable. It is generally preferred to repeat the freeze/thaw cycle from about 0 to about 15 times, and, in vascular graft applications especially, more preferably from about 3 to about 6 times. Most preferably, the freeze/thaw cycle is repeated twice, for a total of three freeze/thaw cycles in the first stage.

After the material has undergone the first stage of freeze/thaw treatment it is carefully removed from the mold in order to avoid damaging the material and immediately submerged in a liquid bath, preferably of deionized, sterile water. The material can be removed from the mold in either thawed or frozen state. Moreover, the material can be removed from either part or the entire mold. For example, it may be suitable to retain the mandrels within the material if an annular mold is employed, to prevent the material from deforming. The bath should be large enough so that the material is immersed completely in water, and can be open or closed, but preferably closed to maintain sterility.

The second stage involves further freeze/thaw treatment of the molded material. After the mixture is immersed in water, it is again subjected to one or more freeze/thaw cycles in the second stage of the processing. Again, the conditions for each freeze/thaw cycle in the second stage need not be identical. The mixture should preferably be frozen and thawed from about 1 to about 15 times, more preferably, especially for vascular graft applications, from 1 to 5 times, and most preferably 4 times, while the mixture is submerged in the water. As in the first stage, increasing the number of freeze/thaw cycles increases the tensile strength and tensile stiffness, and the number of cycles can thus be selected based upon the particular application that is planned for the hydrogel.

The conditions under which the freeze/thaw cycles of the second stage are carried out are generally comparable to the conditions observed in carrying out the first stage. After the mixture has undergone the second stage of freeze/thaw cycles, it is ready for use.

The poly(vinyl alcohol) hydrogel of the present invention can also comprise a bioactive agent to lend to the hydrogel suitable physiological properties for it to be used as a soft tissue replacement. The bioactive agent can be chosen based upon the particular application planned for the replacement, and the particular physiological properties required of the replacement in the application involved. Many such bioactive agents would be released gradually from the hydrogel after implantation, and thereby delivered in vivo at a controlled, gradual rate. The hydrogel can thus act as a drug delivery vehicle. Other bioactive agents can be incorporated in to the hydrogel in order to support cellular growth and proliferation on the surface of the material. Bioactive agents which can be included in the replacement include, for example, growth factors, collagen crosslinking inhibitors such as β-aminopropeonitrile (βAPN) or cis-4-hydroxyproline, matrix inhibitors, antibodies, cytokines, integrins, thrombins, thrombin inhibitors, proteases, anticoagulants, and glycosaminoglycans. Heparins are particularly suitable agents for incorporating into vascular grafts, because of their anticoagulant properties, and thus their ability to inhibit thrombosis on the surface of the hydrogel.

In order to embed heparin or other bioactive agents into the hydrogel of the present invention any of a pre-sterilized heparin powder, aqueous heparin or aqueous heparin suspension can be mixed into the starting sterile poly(vinyl alcohol)/water mixture. After the heparin or other bioactive agent is incorporated into the poly(vinyl alcohol)/water mixture, it is thermally processed along with the poly(vinyl alcohol)/water mixture according to the process described herein. Heparin and other bioactive agents can also be introduced into the hydrogel by placing the hydrogel into a bath containing an aqueous solution of the agent and allowing the agent to diffuse into the hydrogel.

The concentration of the heparin or other bioactive agent in the mixture may be selected for the particular application involved. For heparin incorporation into a vascular graft, concentrations will typically range from 1 unit/ml. to 1,000,000 units/ml. Lower concentrations will be employed to inhibit coagulation on the graft surface, and higher concentrations will be used where local infusion of heparin into the blood is desired to inhibit thrombosis downstream of the graft, as described in Chen et al., *Boundary layer infusion of heparin prevents thrombosis and reduces neointimal hyperplasia in venous polytetrafluoroethylene grafts without systemic anticoagulation,* J. Vascular Surgery, v. 22, pp., 237–247 (1995).

The hydrogel supports the proliferation of eukaryotic cell cultures. Vascular cells such as endothelial cells, smooth muscle cells, and fibroblasts and other connective tissue cells, can thus be incorporated into the hydrogel. Human aortic endothelial cells and human dermal fibroblasts are also compatible with the hydrogels of the present invention. Hydrogels modified by such cell lines are, in turn, especially well adapted for implantation into the human body, and for use as soft tissue replacement parts in the human body. Indeed, replacement parts modified by such cell lines are better able to adapt and adjust to changing physical and physiological conditions in the body, and thereby to prevent any failure of the hydrogel which might otherwise occur. Hydrogels modified by such cell lines are, in sum, especially well adapted for implantation in the human body, and for use as replacement parts in the human body. These cellular lines can be incorporated into the hydrogel, after it has been produced, via standard cell culture protocol generally known in the art. It is especially effective to culture human aortic endothelial cells and human dermal fibroblasts using direct topical seeding and incubation in cell culture medium.

Besides the soft tissue replacement uses set forth for the poly(vinyl alcohol) hydrogel, discussed above, the hydrogels of the present invention can be used in any application in which poly(vinyl alcohol) hydrogels are generally suitable, including as an MR (magnetic resonance) quality control phantom, as an ultrasound or radio frequency thermal therapy transmission pad, as a substitute for an ice bag, as a denture base, and in other medical applications.

Although the following examples set out specific parameters for constructing a PVA hydrogel in accordance with the present invention, the ordinarily skilled artisan will understand that mechanical properties of the PVA hydrogel may be affected by one of four factors. Those factors include: (1) weight percentage of the respective constituents within the hydrogel (e.g. PVA polymer and water); (2) the molecular weight of the PVA starting material; (3) the number of freeze/thaw cycles; and (4) the duration of a freeze cycle. It is also important to note that the freeze/thaw cycle promotes an interlocking mesh or entanglement between molecules of PVA to create the mechanical strength. This is different than the traditional cross link accomplished by the above-referenced cross linking agents which inevitably introduces a toxic agent into the biomaterial, thus decreasing biocompatibility of materials which utilize those cross linking agents.

EXAMPLE 1

A 15% by weight poly(vinyl alcohol) solution was prepared by mixing 17.6 grams of poly(vinyl alcohol) polymer (124,000–186,000 Av. MW), 99+% saponification, in 100 ml of deionized, sterile water. The mixture was placed in a loosely capped container, heated and sterilized at 121° C. and 17 p.s.i. in an autoclave for about 15 minutes. The container was then sealed removed from the autoclave and placed under a sterile ventilation hood. The mixture was then stirred to ensure a homogenous solution. The mixture was poured into sterile syringes, being careful not to generate air bubbles. The poly(vinyl alcohol) solution was then injected upwardly into stainless steel annular molds having stainless steel mandrels. The outer tube of the annulus had an inner diameter of 8 mm which surrounded a 5 mm diameter mandrel. The time that the solution was exposed to air was minimized in order to prevent evaporation of water. The mold was designed to create a poly(vinyl alcohol) hydrogel with approximately a 1.5 mm wall thickness, 10 cm long, having a 5 mm inside diameter. The mold was sealed at both ends using O-rings and rubber caps. Air space, equaling about 8% of the volume of the mold was deliberately maintained in order to allow for expansion while the aqueous solution froze.

The tube was then subjected to three (3) cycles of freezing and thawing. In each of the cycles the tube was frozen by placing it upright in a commercial freezer regulated at about −20° C., and allowing it to air cool for about 12 hours. The tube was then thawed by removing the tube from the freezer and setting it upright under ambient conditions. The tube was allowed to thaw for about 12 hours before being returned to the freezer for another cycle.

After the mixture had been frozen and thawed three times, it was removed from the tube (under a sterile vacuum hood) and immersed in a 50 ml, centrifuge vial containing 35 ml of deionized, sterile water. There was obtained a translucent to clear, gummy, weak material which was substantially unable to maintain its shape outside of water or other liquid. The material was handled carefully with forceps and immersed in water as quickly as possible. The inner diameter of the material was preserved by keeping the inner mandrel in place. The container was then sealed and placed in a freezer at about −20° C. The mixture was kept in the freezer for about 12 hours, and then removed and allowed to stand at room temperature for about 12 hours. The freezing and thawing process was repeated once, thus considering the three previous cycles within the mold, the mixture was subjected to a total of five (5) cycles of freezing and thawing.

The material obtained was opaque, elastic, and non-sticky, with mechanical properties very similar to a native artery tissue. The material was tested for mechanical strength according to standards of the Association for the Advancement of Medical Instrumentation and the American National Standards Institute, published in *Cardiovascular implants—Vascular Prosthesis,* ANSI/AAMI VP20-1994, section 8.3.3.3 (pressurized burst strength), and Section 8.8 (suture retention strength). The material had a burst pressure of about 540 mm Hg. Specifically, a 6-0 suture was placed 2 mm from the edge of the graft and pulled at a rate of 150 mm/min until it pulled through the graft. The average peak pullout load for the material a suture test was about 289 grams, which is greater than the pullout loads reported in the literature for human artery and vein. Finally, the tensile modulus of elasticity of the material was measured to be approximately $4.0 \times 10^5$ Pa.

EXAMPLE 2

A 25.9% by weight poly(vinyl alcohol) solution was prepared by mixing poly(vinyl alcohol) polymer (124,000–186,000 Av. MW), 99+% saponification, in deionized, sterile water. As with Example 1, the mixture was placed in a loosely capped container, heated, sealed removed from the autoclave, placed under a sterile ventilation hood, stirred to ensure a homogenous solution, poured into sterile syringes, and injected into the molds according to the process of Example 1. In this example, however, the tube was then subjected to ten (10) cycles of freezing and thawing. The freeze/thaw cycles were similar to that of Example 1, except that the sample was allowed to cool for about 24 hours for each freeze/thaw cycle. The tube was then thawed by removing the tube from the freezer and setting it upright under ambient conditions. The tube was allowed to thaw for about 12 hours before being returned to the freezer for another cycle. The resulting PVA biomaterial was stiff and strong with a burst pressure of approximately 1078 mm Hg.

EXAMPLE 3

A 15% by weight poly(vinyl alcohol) solution was prepared by mixing poly(vinyl alcohol) polymer (89,000–98,000 Av. MW), 99+% saponification, in deionized, sterile water in a manner substantially identical with Example 1 except for the following differences. As with Example 1, the mixture was placed in a loosely capped container, heated, sealed removed from the autoclave, placed under a sterile ventilation hood, stirred to ensure a homogenous solution, poured into sterile syringes, and injected into the molds according to the process of Example 1. In this example, however, the tube was then subjected to five (5) cycles of freezing and thawing. The freeze/thaw cycles were similar to that of Example 1, in that each sample was allowed to cool for about 12 hours for each freeze/thaw cycle. The resulting PVA biomaterial was soft with a burst pressure of approximately 98 mm Hg.

EXAMPLE 4

A 25–30% by weight poly (vinyl alcohol) solution was prepared by mixing poly (vinyl alcohol) polymer (124,000–186,000 Av. MW) in sterile water or saline (0.9% Na Cl) in a manner substantially identical with Example 1 except for the following differences. The mixture is heated at 95–100° C. under atmospheric pressure to bring the mixture to a uniform fluid. This fluid is then poured into molds and frozen to −20° C. for four hours. Next, the material is thawed to 20° C. This freeze-thaw cycle is repeated until six cycles have been achieved. The material is, at least partially, removed from the mold, immersed, at least in part, and the freeze-thaw cycle is repeated until four additional cycles have been achieved. As an alternative to at least partially removing the material from the mold, the mold may be partially filled with fluid mixture, thereby allowing for expansion. The resultant PVA hydrogel construct is then ready for packaging and sterilization. This process yields a material having a modulus of elasticity (tensile or compression) which is greater than 1.0 mPa. The % by weight and the MW of the PVA can be altered to provide materials with a different modulus of elasticity depending upon the particular medical application.

As demonstrated by the above-referenced examples, because the PVA hydrogel can be manufactured to be mechanically strong, or to possess various levels of strength among other physical properties depending upon the weight percentage of the PVA starting material with respect to other constituents in solution, freeze time, the number of freeze/thaw cycles, and the freeze temperature. As discussed above, the end product hydrogel also has a high water content which provides desirable properties in numerous applications and which prevents the denaturing of additives.

The hydrogel tissue replacement construct is especially useful in surgical and other medical applications as an artificial material for replacing and reconstructing soft tissues in humans and other mammals. Soft tissue body parts which can be replaced or reconstructed by the hydrogel include, but are not limited to, vascular grafts, heart valves, esophageal tissue, skin, corneal tissue, ureternal stents, nerve bridge, wound covering cartilage, meniscus, and tendon. The hydrogel may be formed as an implantable articulating surface for a load bearing joint, whereby the articulating surface may be fixed to bone with screws, sutures, or bioglue such as a collagenglue. Furthermore, the hydrogel may also serve as a cartilage replacement for anatomical structures including, but not limited to an ear or nose.

The inventive hydrogel may also serve as a tissue expander. Additionally, the inventive hydrogel may be suitable for an implantable drug delivery device. In that application, the rate of drug delivery to tissue will depend upon hydrogel pore size and degree of intermolecular meshing resulting from the freeze/thaw cycles. The rate of drug delivery increases with the number of pores and decreases with an increasing degree of intermolecular meshing from an increased number of freeze/thaw cycles.

The hydrogel is especially suitable for vascular grafts and heart valve replacements, because the hydrogel is thromboresistant, and because of the particular mechanical and physiological requirements of vascular grafts when implanted into the body. The hydrogel may also be used for contact lenses, as a covering for wounds such as burns and abrasions, and in other applications wherein a mechanically strong material is preferred.

Throughout this application, various publications are referenced. The disclosures of these publications in their entireties are hereby incorporated by reference into this application in order to more fully describe the state of the art to which this invention pertains.

The foregoing description has been presented for purposes of illustration and description. It is not intended to be exhaustive or to limit the invention to the precise examples or embodiments disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A poly(vinyl alcohol) (PVA) construct consisting essentially of:

a PVA polymer; and saline;

said construct having a compressive modulus of elasticity of between about 0.5 megaPascals and about 10 megaPascals and a glass transition temperature greater than 40° C., said construct being further defined as having been prepared according to the following steps:

pouring an aqueous PVA polymer mixture into a mold;

freezing and thawing said PVA polymer mixture within said mold at least once to create an interlocking mesh between PVA polymer molecules to create the semi-crystalline organic hydrogel;

allowing for expansion of said PVA hydrogel within said mold;

immersing said PVA hydrogel in an aqueous solution; and freezing and thawing said PVA hydrogel at least once while immersed in water.

2. A biocompatible hydrogel joint resurfacing agent comprising:

a semi-crystalline organic polymer; and a water content greater than about 20% by weight;

said hydrogel having a compressive modulus of elasticity of between about 0.5 megaPascals and about 10 megaPascals and a glass transition temperature greater than 40° C., said construct being further defined as having been prepared according to the following steps:

pouring an aqueous semi-crystalline organic polymer mixture into a mold;

freezing and thawing said semi-crystalline organic polymer mixture within said mold at least once to create an interlocking mesh between semi-crystalline organic polymer molecules to create the semi-crystalline organic polymer hydrogel;

allowing for expansion of said semi-crystalline organic polymer hydrogel, at least partially within said mold;

immersing said semi-crystalline organic polymer hydrogel in an aqueous solution; and freezing and thawing said semi-crystalline organic polymer hydrogel at least once while immersed in water.

3. The biocompatible hydrogel of claim 2 which further contains eukaryotic cells.

4. The PVA hydrogel of claim 3, wherein said eukaryotic cells are selected from the group consisting of: endothelial cells, aortic endothelial cells, smooth muscle cells, fibroblasts, dermal fibroblasts, and connective tissue cells.

5. The biocompatible hydrogel of claim 2 which further contains radioisotopes.

* * * * *